(12) United States Patent
Maitland et al.

(10) Patent No.: US 7,291,154 B2
(45) Date of Patent: Nov. 6, 2007

(54) SHAPE MEMORY POLYMER ACTUATOR AND CATHETER

(75) Inventors: Duncan J. Maitland, Pleasant Hill, CA (US); Abraham P. Lee, Walnut Creek, CA (US); Daniel L. Schumann, Concord, CA (US); Dennis L. Matthews, Moss Beach, CA (US); Derek E. Decker, Byron, CA (US); Charles A. Jungreis, Pittsburgh, PA (US)

(73) Assignee: The Regents of the University of California, Oakland, CA (US)

( * ) Notice: Subject to any disclaimer, the term of this patent is extended or adjusted under 35 U.S.C. 154(b) by 747 days.

(21) Appl. No.: 10/713,622

(22) Filed: Nov. 13, 2003

(65) Prior Publication Data

US 2004/0133231 A1 Jul. 8, 2004

Related U.S. Application Data

(62) Division of application No. 09/761,023, filed on Jan. 16, 2001, now Pat. No. 6,740,094.

(60) Provisional application No. 60/246,293, filed on Nov. 6, 2000.

(51) Int. Cl.
*A61F 11/00* (2006.01)

(52) U.S. Cl. .................................................. 606/108
(58) Field of Classification Search .................. 606/1, 606/108, 205–210, 211, 151, 157, 198, 191; 604/93.01, 164.03, 164.13
See application file for complete search history.

(56) References Cited

U.S. PATENT DOCUMENTS

| 4,919,133 A | 4/1990 | Chiang |
| 6,102,932 A * | 8/2000 | Kurz ........................... 606/200 |
| 6,296,622 B1 * | 10/2001 | Kurz et al. .................. 606/198 |
| 2002/0072764 A1 | 6/2002 | Sepetka et al. |

FOREIGN PATENT DOCUMENTS

| WO | WO 92 16153 | 10/1992 |
| WO | WO 00 30523 | 6/2000 |

* cited by examiner

*Primary Examiner*—Kevin T. Truong
(74) *Attorney, Agent, or Firm*—Eddie E. Scott; John H. Lee

(57) ABSTRACT

An actuator system is provided for acting upon a material in a vessel. The system includes an optical fiber and a shape memory polymer material operatively connected to the optical fiber. The shape memory polymer material is adapted to move from a first shape for moving through said vessel to a second shape where it can act upon said material.

4 Claims, 11 Drawing Sheets

SHAPE MEMORY POLYMER ACTUATOR AND CATHETER

REFERENCE TO PROVISIONAL APPLICATION TO CLAIM PRIORITY

This application claims the benefit under 35 U.S.C. § 119(e) of U.S. provisional patent application No. 60/246,293, filed Nov. 6, 2000, which is hereby incorporated by reference in its entirety.

CROSS-REFERENCE TO RELATED APPLICATION

This application is a division of application Ser. No. 09/761,023 entitled "Shape Memory Polymer Actuator and Catheter," filed Jan. 16, 2001 now U.S. Pat. No. 6,740,094.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to actuators and in particular to a shape memory polymer actuator.

2. State of Technology

U.S. Pat. No. 5,836,868 for an expandable intravascular occlusion material removal devices and methods of use, by Ressemann et al, patented Nov. 17, 1998, provides the following description: "The present invention generally relates to constructions for intravascular treatment devices useful for removing vascular occlusion material from a vascular occlusion or from a vascular lumen. The invention more specifically relates to expandable intravascular occlusion material removal devices, as well as to methods of using those devices to treat vascular diseases.

Vascular diseases, such as atherosclerosis and the like, have become quite prevalent in the modern day. These diseases may present themselves in a number of forms. Each form of vascular disease may require a different method of treatment to reduce or cure the harmful effects of the disease. Vascular diseases, for example, may take the form of deposits or growths in a patient's vasculature which may restrict, in the case of a partial occlusion, or stop, in the case of a total occlusion, blood flow to a certain portion of the patient's body. This can be particularly serious if, for example, such an occlusion occurs in a portion of the vasculature that supplies vital organs with blood or other necessary fluids.

To treat these diseases, a number of different therapies are being developed. While a number of invasive therapies are available, it is desirable to develop non-invasive therapies as well. Non-invasive therapies may be less risky than invasive ones, and may be more welcomed by the patient because of the possibility of decreased chances of infection, reduced post-operative pain, and less post-operative rehabilitation. One type of non-invasive therapy for vascular diseases is pharmaceutical in nature. Clot-busting drugs have been employed to help break up blood clots which may be blocking a particular vascular lumen. Other drug therapies are also available. Further non-invasive, intravascular treatments exist that are not only pharmaceutical, but also revascularize blood vessels or lumens by mechanical means. Two examples of such intravascular therapies are balloon angioplasty and atherectomy which physically revascularize a portion of a patient's vasculature.

Balloon angioplasty comprises a procedure wherein a balloon catheter is inserted intravascularly into a patient through a relatively small puncture, which may be located proximate the groin, and intravascularly navigated by a treating physician to the occluded vascular site. The balloon catheter includes a balloon or dilating member which is placed adjacent the vascular occlusion and then is inflated. Intravascular inflation of the dilating member by sufficient pressures, on the order of 5 to 12 atmospheres or so, causes the balloon to displace the occluding matter to revascularize the occluded lumen and thereby restore substantially normal blood flow through the revascularized portion of the vasculature. It is to be noted, however, that this procedure does not remove the occluding matter from the patient's vasculature, but displaces it.

While balloon angioplasty is quite successful in substantially revascularizing many vascular lumens by reforming the occluding material, other occlusions may be difficult to treat with angioplasty. Specifically, some intravascular occlusions may be composed of an irregular, loose or heavily calcified material which may extend relatively far along a vessel or may extend adjacent a side branching vessel, and thus are not prone or susceptible to angioplastic treatment. Even if angioplasty is successful, thereby revascularizing the vessel and substantially restoring normal blood flow therethrough, there is a chance that the occlusion may recur. Recurrence of an occlusion may require repeated or alternative treatments given at the same intravascular site.

Accordingly, attempts have been made to develop other alternative mechanical methods of non-invasive, intravascular treatment in an effort to provide another way of revascularizing an occluded vessel and of restoring blood flow through the relevant vasculature. These alternative treatments may have particular utility with certain vascular occlusions, or may provide added benefits to a patient when combined with balloon angioplasty and/or drug therapies.

One such alternative mechanical treatment method involves removal, not displacement, as is the case with balloon angioplasty, of the material occluding a vascular lumen. Such treatment devices, sometimes referred to as atherectomy devices, use a variety of means, such as lasers, and rotating cutters or ablaters, for example, to remove the occluding material. The rotating cutters may be particularly useful in removing certain vascular occlusions. Since vascular occlusions may have different compositions and morphology or shape, a given removal or cutting element may not be suitable for removal of a certain occlusion. Alternatively, if a patient has multiple occlusions in his vasculature, a given removal element may be suitable for removing only one of the occlusions. Suitability of a particular cutting element may be determined by, for example, its size or shape. Thus, a treating physician may have to use a plurality of different treatment devices to provide the patient with complete treatment. This type of procedure can be quite expensive because multiple pieces of equipment may need to be used (such intravascular devices are not reusable because they are inserted directly into the blood stream), and may be tedious to perform because multiple pieces of equipment must be navigated through an often-tortuous vascular path to the treatment site."

U.S. Pat. No. 5,102,415, for an apparatus for removing blood clots from arteries and veins, by Guenther et al, patented Apr. 7, 1992, provides the folowing description: "A triple catheter for removing of blood clots from arteries and veins is equipped with an outer catheter that can be inserted into a blood vessel and an inner catheter with an inflatable baloon at its distal end that can be inserted into the outer catheter. The inner catheter is surrounded by an intermediate catheter also inserted into the outer catheter. The intermediate catheter has a radially expandable distal end receptacle made of an elastic mesh structure of spring wires or plastic monofilaments covered by or embedded in an elastic plastic coating. A very small puncture channel is required for the insertion of such a triple catheter through the wall of a blood vessel."

U.S. Pat. No. 5,645,564 for microfabricated therapeutic actuator mechanisms, by Northrup et al, patented Jul. 8, 1997, provides the folowing description: "Electromechanical microstructures (microgrippers), either integrated circuit (IC) silicon-based or precision machined, to extend and improve the application of catheter-based interventional therapies for the repair of aneurysms in the brain or other interventional clinical therapies. These micromechanisms can be specifically applied to release platinum coils or other materials into bulging portions of the blood vessels also known as aneurysms. The "micro" size of the release mechanism is necessary since the brain vessels are the smallest in the body. Through a catheter more than one meter long, the micromechanism located at one end of the catheter can be manipulated from the other end thereof. The microgripper (micromechanism) of the invention will also find applications in non-medical areas where a remotely actuated microgripper or similar actuator would be useful or where micro-assembling is needed."

U.S. Pat. No. 6,102,917 for a shape memory polymer (SMP) gripper with a release sensing system, by Maitland et al, patented Aug. 15, 2000, provides the following description: "A system for releasing a target material, such as an embolic coil from an SMP located at the end of a catheter utilizing an optical arrangement for releasing the material. The system includes a laser, laser driver, display panel, photodetector, fiber optics coupler, fiber optics and connectors, a catheter, and an SMP-based gripper, and includes a release sensing and feedback arrangement. The SMP-based gripper is heated via laser light through an optic fiber causing the gripper to release a target material (e.g., embolic coil for therapeutic treatment of aneurysms). Various embodiments are provided for coupling the laser light into the SMP, which includes specific positioning of the coils, removal of the fiber cladding adjacent the coil, a metal coating on the SMP, doping the SMP with a gradient absorbing dye, tapering the fiber optic end, coating the SMP with low refractive index material, and locating an insert between the fiber optic and the coil."

U.S. Pat. No. 5,843,118 for fibered micro vaso-occlusive devices, by Sepetka et al, patented Dec. 1, 1998, provides the following description: "This is a vaso-occlusive device made up of at least one short retainer and a longer fiber bundle. The retainer may be radio-opaque. The fibers may be straight, looped, or tufted. The primary use of the device is in the very small vessels at the distal portion of the vasculature."

U.S. Pat. No. 5,895,398 for a method of using a clot capture coil, by Wensel et al, patented Apr. 20, 1999, provides the following description: "A clot and foreign body removal device is described which comprises a catheter with at least one lumen. Located within the catheter is a clot capture coil that is connected to an insertion mandrel. In one embodiment, the clot capture coil is made out of a solid elastic or superelastic material which has shape memory, preferably nitinol. The elasticity or superelasticity of the coil allows it to be deformed within the catheter and to then reform its original coil configuration when the coil is moved outside of the catheter lumen. In another embodiment the coil is a biphasic coil which changes shape upon heating or passing an electric current. Once the coil configuration has been established, the coil can be used to ensnare and corkscrew a clot in a vessel. A clot is extracted from the vessel by moving the clot capture coil and catheter proximally until the clot can be removed or released into a different vessel that does not perfuse a critical organ. Foreign bodies are similarly captured by deploying the coil distal to the foreign body and moving the clot capture coil proximally until the foreign body is trapped within the coil. By removing the device from the body, the foreign material is also removed."

SUMMARY OF THE INVENTION

The present invention provides an actuator system. The system uses heat to activate a shape memory material. The shape memory material will change shape when heated above a transition temperature. The shape memory material is adapted to move from a first shape to a second shape where it can perform a desired function. In one embodiment of the present invention a method of removing matter from a vessel is described. A catheter with a shape memory material is transported to the site of the matter to be removed. The shape memory material is passed through or around the matter. Heat is utilized to activate the shape memory material and expand the shape memory material. By withdrawing the catheter and the shape memory material through said vessel the matter is carried from the vessel. Additional aspects, advantages, and features of the invention are set forth in part in the following description. Various aspects, advantages, and features of the invention will become apparent to those skilled in the art upon examination of the description and by practice of the invention.

BRIEF DESCRIPTION OF THE DRAWINGS

The accompanying drawings, which are incorporated into and form a part of the disclosure, illustrate embodiments of the invention, and, together with the description, serve to explain the principles of the invention.

DETAILED DESCRIPTION OF THE INVENTION

Figure 1:
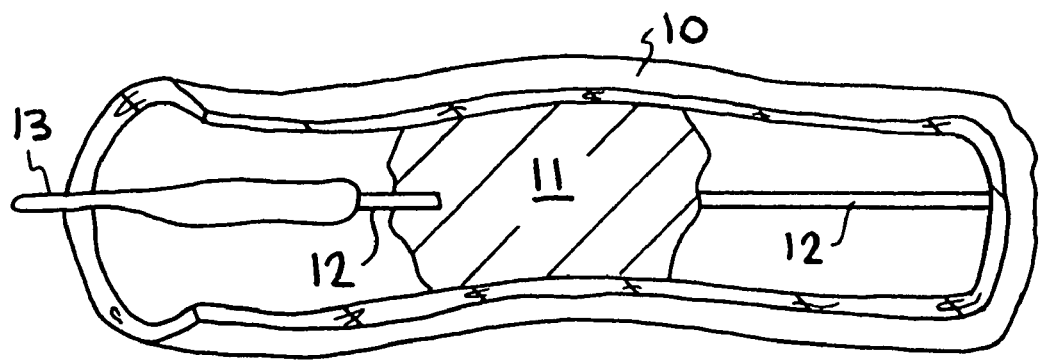
FIG. 1 is a conceptual illustration of an embodiment of the present invention in a vessel with a blockage such as a blood clot.
Figure 2:
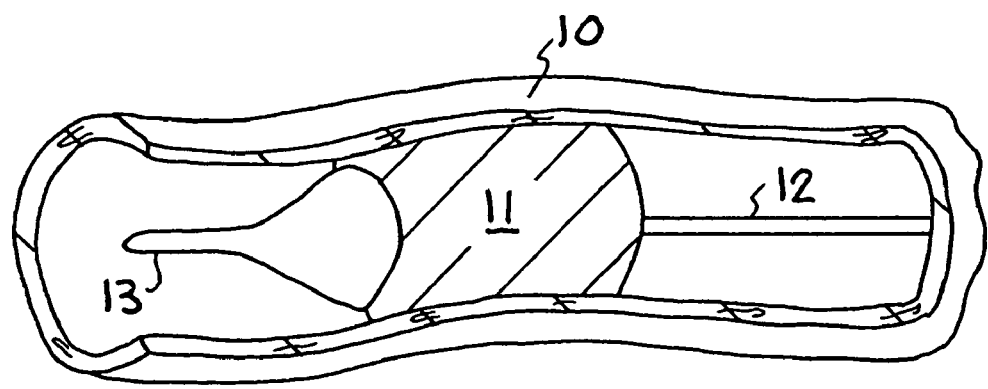
FIG. 2 is a conceptual illustration of an embodiment of the present in a vessel in an expanded position.
Figure 3:
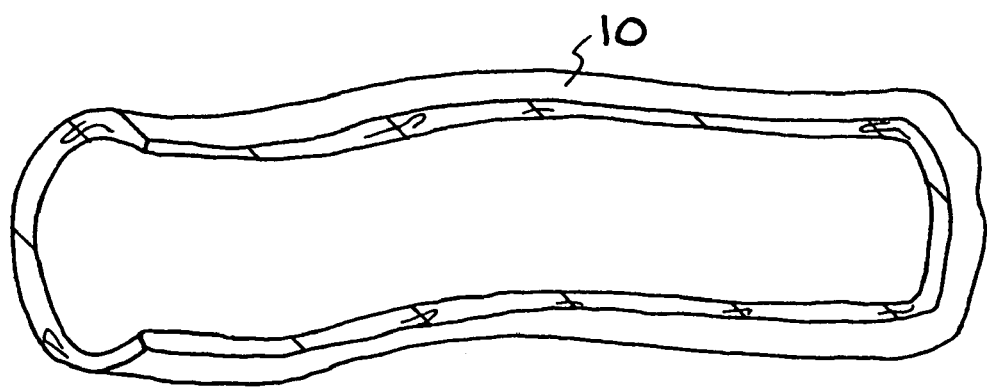
FIG. 3 is a conceptual illustration showing that when the shape memory material actuator is drawn backward it results in removal of the blockage.

Referring now to the drawings, and in particular to FIGS. 1, 2, and 3 of the drawings, a medical application of an embodiment of an actuator constructed in accordance with the present invention is illustrated. Although a specific application of the present invention is described, it is to be understood that the invention is intended to be general in nature, and can be employed wherever actuators are needed. The methods and devices are general to all applications of actuation and control of a shaped memory material.

The present invention provides an actuator system. The system uses heat to activate a shape memory material. The shape memory material will change shape when heated above a transition temperature. The shape memory material is adapted to move from a first position to a second position where it can perform a desired function. In this embodiment of the present invention a method of removing matter from a vessel is described. A catheter with a shape memory material is transported to the site of the matter to be removed. The shape memory material is passed through or around the matter. Heat is utilized to activate the shape memory material and expand the shape memory material. By withdrawing the catheter and the shape memory material through said vessel the matter is carried from the vessel. The present invention can be used to remove blockages from many luminal structures.

The shape memory material can be heated using various systems. For example, the shape memory material can be heated as described in U.S. Pat. No. 5,911,737 for microfabricated therapeutic actuators, by Lee et al, patented Jun. 15, 1999 as follows: "Heating of the SMP tubing 20 can be accomplished via induced resistive heating of the end 22 of object 21 by an external wave field, such as by an associated magnetic or radio frequency (RF) source, provided of cause that the end 22 of object 21 is constructed of material inductive of resistance heating. External heating of the end 22 of object 21 can be carried out through electrical induction or electrothermal heating (through a dielectric lossy material on the end of the coil). An example is by applying an external alternating magnetic field to Ni—Pd material coated on at least the end 22 of object or coil 21." The disclosure of U.S. Pat. No. 5,911,737 is incorporated herein by reference. The shape memory material can also be heated using an optical system. The system uses energy in the form of light guided by an optical fiber to a light, diffusing device that radiates the light into the shape memory material. The light is absorbed by the shape memory material and converted into heat.

FIG. 1 shows a vessel 10 with a blockage 11. The blockage could be a blood clot, plaque, other emboli, or other blockage. A support structure 12 with a shape memory material actuator 13 on its distal end is inserted through or around the blockage 11. The shape memory material actuator 13 is used to remove the blockage 11 from the vascular system.

FIG. 2 shows the expanded shape memory material actuator 13. Actuation is achieved by heating the shape memory material. The shape memory material can be heated using various systems. These systems include induced resistive heating by an external wave field, such as by an associated magnetic or radio frequency (RF) source, external heating through electrical induction or electrothermal heating, with local or remote ultrasonics or other acoustic means of energy transfer, or by converting optical energy into thermal energy that allows the stored energy in the shape memory material to be released. The heating of the SMP can be accomplished by an operatively connected or embedded mechanism which is powered by the absorption of applied energy in the form of light, electric fields, magnetic fields, RF fields, EM waves, acoustic/ultrasound waves, electric current flow (DC: resistive heating, AC: inductive or dielectric heating), chemical reactions and/or other heating mechanisms such as nuclear heating ect. The optical energy is absorbed by the shape memory material and converted into thermal energy that heats the shape memory material above its transition temperature and the shape memory material moves to its primary shape, resulting in opto-mechanical actuation.

FIG. 3 shows that, when the shape memory material actuator is drawn backward it results in the removal of the blockage from the vessel 10. The catheter with the shape memory material 13 was transported to the site of the matter 11 to be removed. The shape memory material 13 was passed through or around the matter 11. Heat was utilized to activate the shape memory material 13 and expand the shape memory material 13. By withdrawing the support structure 12 and the shape memory material 13 through the vessel 10 the matter 11 was carried from the vessel 10.

The shape memory material actuator system has significant utility, for example, the treatment cost of ischemic strokes is estimated to be $20 Billion/year. The support structure 12 shown in FIGS. 1 and 2 uses an expanding opto-mechanical actuator system. The system uses energy in the form of light guided by an optical fiber to a light diffusing device that radiates the light into the shape memory material. The light is absorbed by the shape memory material and converted into heat. The shape memory material will change shape when heated above a transition temperature.

Figure 4:
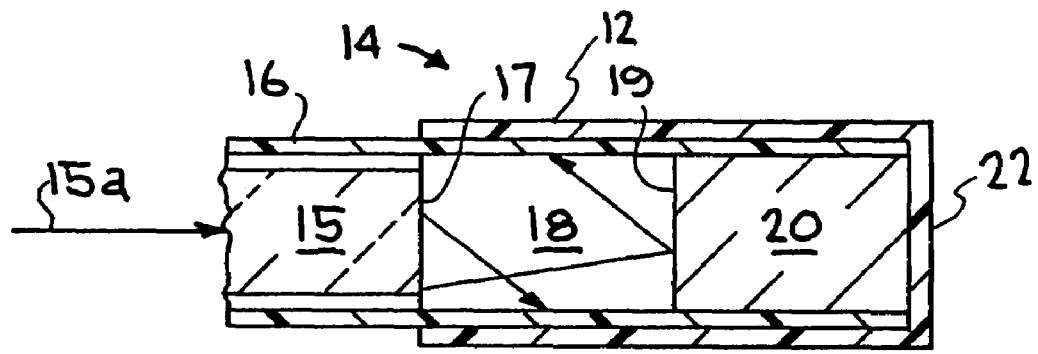
FIG. 4 shows an embodiment of a shape memory polymer actuator in its loaded state.
Figure 5:
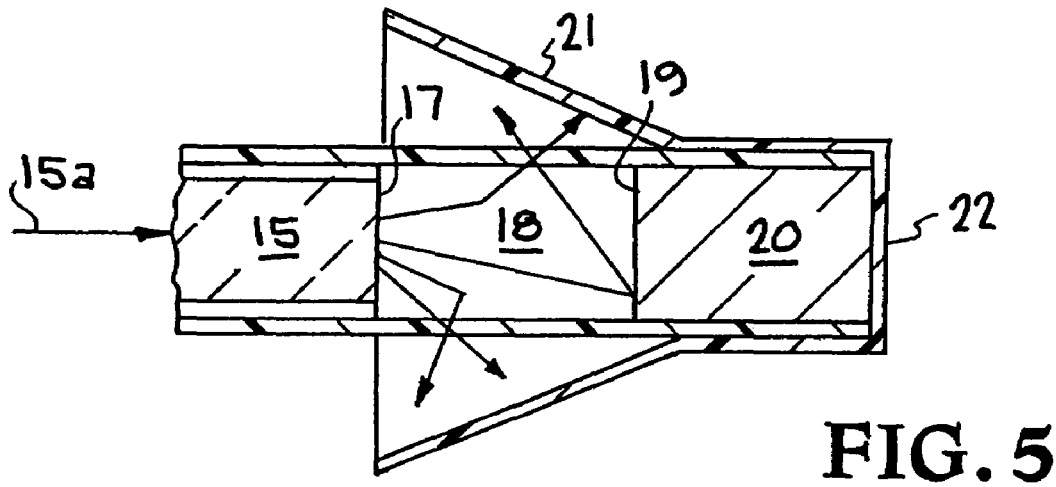
FIG. 5 shows an embodiment of a shape memory polymer actuator in its expanded state.

Referring now to FIGS. 4 and 5, a shape memory material, specifically a shape memory polymer (SMP), SMP actuator system constructed in accordance with the present invention is schematically illustrated. The shape memory polymer (SMP) actuator system is designated generally by the reference numeral 14. The system 14 is an opto-mechanical system that, similar to a guide wire that is commonly pushed through the blood clot, is fed through or around the clot and then actuated to open like an umbrella. The expanded opto-mechanical device is retracted and the blockage is removed. The system includes the following components:

Optical Fiber 15—The optical fiber 15 is typically sheathed in a buffer jacket 16 with additional material layers built up to form a biocompatible catheter. The fiber is multimode with typical core dimensions between 50-1000 µm. The distal end 17 of the fiber 15 delivers light to a diffusing chamber 18.

Optical Source—The optical source 15a provides light energy through the optical fiber 15. The optical source 15a can be a light source coupled into an optical fiber. The light is radiated from the light source. The light is transmitted by the optical fiber 15 to the diffusing device. The diffusing device transmits the light to the shape memory material. The optical source 15a can be various systems. For example, the optical source 15a can be heated as described in U.S. Pat. No. 6,102,917, by Maitland et al, patented Aug. 15, 2000, as follows: "The catheter section 11, extension section 14, and control unit 15 are interconnected by optic fiber connectors 16 and 17. Control unit 15 includes a laser 18, laser control or driving electronics and display panel assembly generally indicated at 19, and connected as indicated at 20 to laser 18. Laser 18 is connected by optic fibers 21 and 22 via an optic fiber connector 23 to a fiber optic coupler 24, such as a conventional 90/10 optical coupler, which is connected via an optic fiber 25 to optic fiber connector 17. Coupler 24, wherein 90 percent of the light passes through and 10 percent is bypassed, is also connected by an optic fiber 26 to a sensing photodetector 27, which is connected to the display panel section of assembly 19 as indicated at 28. Coupler 24 is also connected by an optic fiber 29 to a source photodetector 30, which is connected to the driving electronics or control section of assembly 19, as indicated at 31. Laser light (pulsed or continuous) from laser 18 is transmitted, as indicated by pulses and arrows 32, through optic fiber 21, connector 23, optic fiber 22, coupler 24, optic fiber 25, connector 17, an optic fiber 14' in extension section 14, connector 16, and an optic fiber 11' in catheter section 11 onto an end section of SMP microgripper 12, which retains the coil 13, causing heating of the material of microgripper 12 located around the coil." The disclosure of U.S. Pat. No. 6,102,917 is incorporated herein by reference.

Diffusing Chamber 18—The diffusing chamber 18 distributes the light evenly around the circumference of the chamber and along the chamber length. The distal end 19 of the chamber is terminated with a reflective coating or plug 20 that maximizes the amount of light in the chamber. Typical lengths of the diffusing chamber are 100-5000 µm. A translucent plastic which scatters light is one example of material that could be used in the diffusing chamber.

Shape Memory Polymer (SMP) 21—SMP materials are well known. For example, U.S. Pat. No. 6,086,599 for micro devices using shape memory polymer patches for mated connections, by Lee et al, patented Jul. 11, 2000, states: "SMP material is known in the art, and has been recently utilized as delivery means for medical or non-medical devices to inaccessible locations, such as blood vessels or inside a machine or tubing system." U.S. Pat. No. 5,911,737 for microfabricated therapeutic actuators, by Lee et al, patented Jun. 15, 1999 describes a SMP material as follows: "The SMP material, a polyurethane-based material that undergoes a phase transformation at a temperature (Tg). The SMP material can be constructed so as to be inert to any fluids of the human body, for example, and can be constructed to be responsive to various desired phase transformation temperatures, Tg, above which the material is soft and reshapable and then by cooling the material below the Tg, the material retains the reshaped configuration until it is again heated to above the Tg temperature at which time the SMP material returns to its original memory shape." U.S. Pat. No. 6,102,917 for a shape memory polymer (SMP) gripper with a release sensing system, by Maitland et al, patented Aug. 15, 2000, describes a SMP material as follows: "SMP, a polyurethane-based material that undergoes a phase transformation at a temperature (Tg) of choice.

After the material is polymerized (cross-linked), the material is molded into its memory shape. At temperatures above Tg, the material can be easily reshaped into another configuration, and upon cooling below the Tg the new shape is fixed, but upon increasing the temperature to above the Tg, the material will return to its original memory shape." U.S. Pat. No. 5,189,110 for a shape memory polymer resin, composition and the shape memorizing molded product thereof, by Ikematu et al, patented Feb. 23, 1993, provides the following description: "A shape memory polymer resin, consisting essentially of a block copolymer having an A-B-A block structure in the polymer chain, and having an average molecular weight within the range of 10,000 to 1,000,000, wherein (a) block A is a polymer block comprising a homopolymer or a copolymer of a vinyl aromatic compound and/or a hydrogenated product thereof; (b) block B is a polymer block comprising a homopolymer or a copolymer of butadiene and/or a hydrogenated product thereof, the content of butadiene and/or the hydrogenated product thereof in block B being at least 80% by weight, and 80 to 91% of the linkages of the butadiene and/or the hydrogenated product thereof being 1,4-linkages; (c) at least 80% by weight of the conjugated diene in the block copolymer being hydrogenated; and (d) the block copolymer comprises 5 to 50% by weight of said block A; and a shape memory resin composition and a shape memorizing molded product thereof." The patents identified in this paragraph are incorporated herein by reference.

The SMP 21 is attached to the outer fiber optic layer at its distal end 22. When light from the diffusing chamber 18 is absorbed in the SMP 21 the polymer is heated and the proximal end relaxes to its primary shape. The primary shape of the SMP 21 is formed by heating the SMP 21 above its melting temperature as in an extrusion or molding processes. Typical lengths for the active region of the SMP are 100-5000 µm. The typical angle of the expanded SMP is between 0-90 degrees; however the angle could be beyond 90 degrees up to 180 degrees.

This embodiment focuses on the opto-mechanical methods and design necessary to develop a shape memory polymer (SMP) actuator 14 capable of removing blockages from a lumen. SMP actuation is based on the unique property of the shape memory polymer. This polymer possesses a glass transformation temperature ($T_g$) above which the material enters a reversible glassy phase where it becomes soft and flexible and easy to reshape the material. Once cooled below $T_g$, the shape is frozen in place and the material becomes hardened to over 200 times the elastic modulus of the glassy phase. The reshaped SMP can be used to hold its shape until it is intentionally relaxed by heating the SMP above $T_g$ again.

The system uses energy in the form of light guided by an optical fiber to a light diffusing device that radiates the light into the shape memory polymer. The light is absorbed by the shape memory polymer and converted into heat. The shape memory polymer will change shape when heated above a transition temperature. When light from the diffusing chamber is absorbed in the SMP the polymer is heated and the proximal end relaxes to its primary shape. The primary shape of the SMP is formed by heating the SMP above its melting temperature as in extrusion or molding processes. The SMP can be made by mold injection under vacuum. The mold used is a three part mold. The mold includes one male and two female sections. It is understood that the optical fiber 17 and diffusing chamber 18 are part of the shape memory polymer (SMP) actuator system 14 and these details will not be described in connection with additional embodiments of the present invention.

Figure 6:
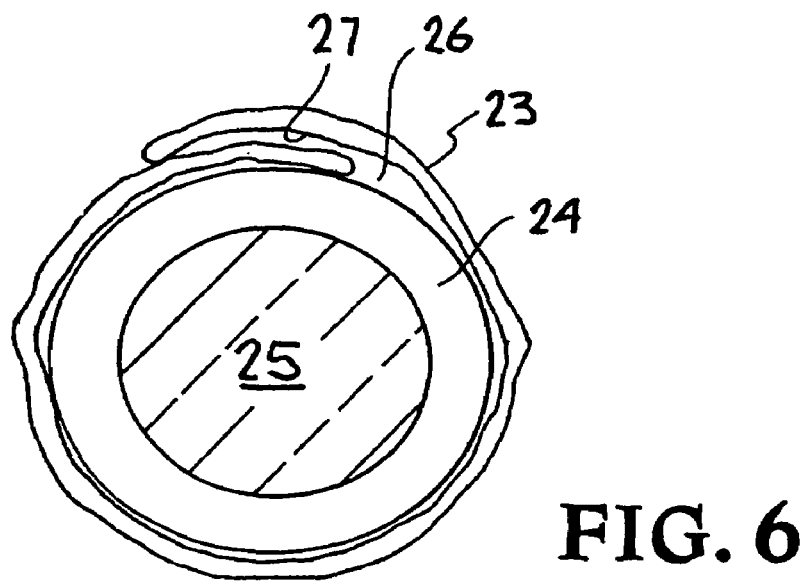
FIG. 6 is a schematic illustration showing the cross section of a closed shape memory polymer actuator.

Referring again to the drawings, FIG. 6 is a schematic illustration showing a closed SMP actuator in its pre-expanded shape for an embodiment of the present invention. One issue with creating a working device is the method of collapsing the SMP such that it fills a minimum volume. In this embodiment, the closed design and the method creating the closed state are linked.

The SMP 23 was sliced along its length and then the SMP was wound around the diffusing chamber 24. In order to create the loaded state, a tube approximately twice the diameter of the fiber was pushed over the SMP 23 and simultaneously turned. This process was carried out in heated water that kept the SMP 23 above its transition temperature, Tg. The SMP 23 was heated using 1 Watt from a 800 nm diode laser coupled into a 1 mm-core optical fiber. Prior to the laser being turned on, the SMP 23 is closed around the diffusing chamber 24. After the laser is turned on, light energy transmitted through the optical fiber 25 will cause the SMP 23 to open.

The closed SMP 23 of the present invention can contain thrombolytic agents 26 that are released at the blockage site when the SMP actuator is opened. These agents can be liquid 26 held in the SMP 23 or coatings on the inner side 27 of the SMP 23 material. The closed state is shown in FIG. 6. The SMP 23 can be meshed or otherwise have holes in it such that as a blockage volume fills the opened SMP 23, the fluid 26 inside is displaced through the mesh. The expanded SMP 23 can form a chamber to collect more blockage material.

Figure 7:
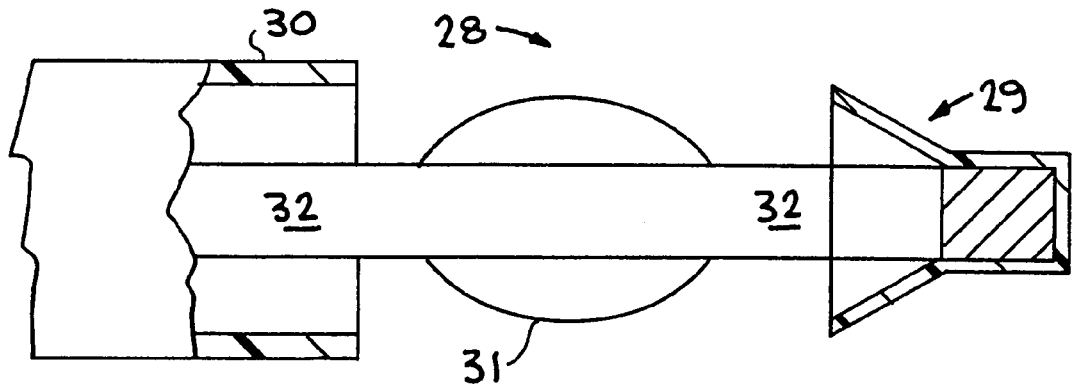
FIG. 7 shows the shape memory polymer actuator used in conjunction with a guide tube (catheter).

Referring now to FIGS. 7, 8, 9, and 10, embodiments of the SMP actuator system of the present invention are illustrated. The SMP actuator system is generally designated by the reference numeral 28. As shown in FIG. 7, the actuator 29 is used in conjunction with a guide tube (catheter) 30 where the expanded actuator 29 with blockage material may be either locked around the guide tube 30, with the whole assembly retracted from the lumen, or pulled through the guide tube 30. A centering device 31 is added to the optic fiber 32 just proximal to the SMP actuator 29. This centering device 31 assists in guiding the expanded actuator 29 back into the guide tube 30 when the fiber optic core 32 is retracted relative to guide tube 30.

Figure 8:
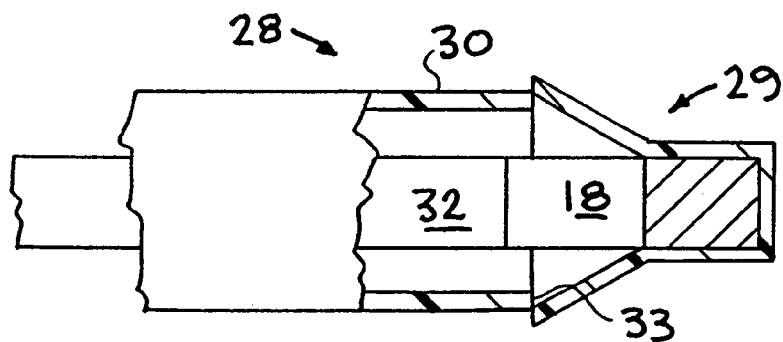
FIG. 8 shows the shape memory polymer actuator used in conjunction with a guide tube (catheter).
Figure 9:
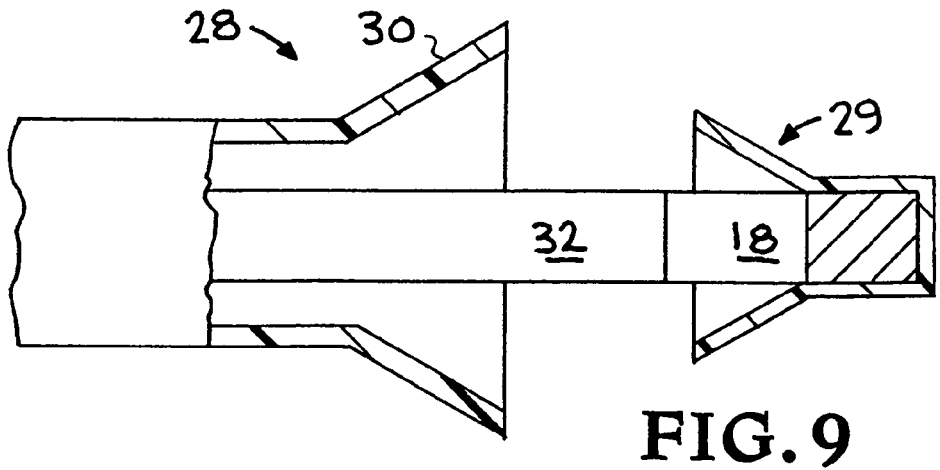
FIG. 9 shows the shape memory polymer actuator used in conjunction with a guide tube (catheter).

As shown by the embodiment of FIG. 8, the guide tube 30 and expanded actuator 29 are made such they can mechanically lock. This locking mechanism may be active as in the case of the distal tip 33 of the guide tube 30 being an SMP actuator itself. In this case, the locking mechanism may also be constructed out of SMP material (e.g. a second SMP that contracts around the expanded "umbrella" actuator). As shown in FIG. 9, the guide tube (catheter) 30 may be flared at its distal tip to easily accept the expanded actuator 29. This enables collapsing the SMP actuator 29.

The SMP actuator 29 of the present invention can contain thrombolytic agents that are released at the blockage site when the SMP actuator 29 is opened. These agents can be liquid held in the SMP or coatings on the inner side of the SMP material.

Figure 10:
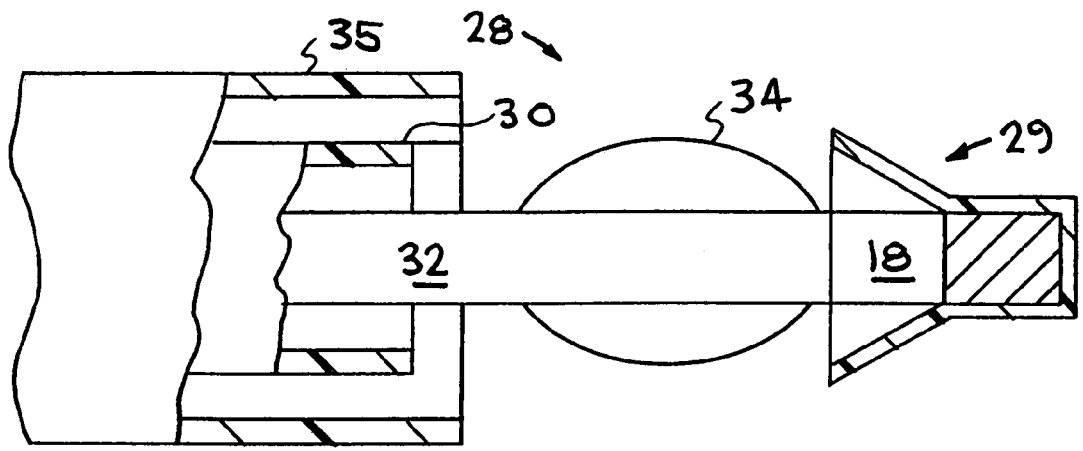
FIG. 10 shows the shape memory polymer actuator used in conjunction with a guide tube (catheter).

Dye may be added to the SMP. Since the light absorption in the SMP actuator 29 facilitates the conversion from optical to thermal energies, the dye concentration may be adjusted so that the light is optimally absorbed in the SMP actuator. Variations of the dye concentration can be used to control heating uniformity and efficiency. Parameters that can be used to control the absorption is dye type, concentration, z-axis (along the length of the fiber) dye gradient, the p-axis distribution (around the circumference of the SMP), and r-axis (through the thickness of the SMP) dye gradient. As shown in the embodiment of FIG. 10, the SMP actuator 29 and optical fiber 32 are carried by a delivery catheter 30. The delivery catheter 30 is contained in a guide catheter 35.

The method of use of the actuator 29 is generally described as working in conjunction with a tube that both delivers the actuator to the blockage and works with the actuator to reshape or remove blockages. The basic design with the addition of a hollow balloon or centering device 34 is shown in the embodiment of FIG. 10. If the whole assembly (guide tube and actuator) is to be utilized, then the method may employ a mating between the tube and actuator as shown in the embodiment of in FIG. 8. Alternatively, the device may be optimally used if the guide tube remains in place while the actuator (and other devices) is removed through the tube. Features that enable this are a flared distal tip shown in the embodiment of FIG. 9 and the centering device shown in FIG. 7, that both may be SMP actuators in and of themselves. Devices can either contain the clot remotely, i.e., at the site of the SMP umbrella, or by retracting it into a docking stand at the distal end of a delivery or "tracker" catheter 30 shown in the embodiment of FIG. 10. Remote capture is desired because the guide catheter is difficult, if not impossible, to pass through the carotid sinus or bulb. The docking stand can be accomplished by either using an activatable SMP flaring device such as shown in the embodiment of FIG. 9 or by using a hollow inflatable balloon 34 such as shown in the embodiment of FIG. 10. Also note that the balloon concept could be used provide a local cap or lid on the proximal end of the SMP umbrella clot catcher while also providing a means to center the device upon retracting into the delivery or "tracker" catheter 30.

Figure 11:
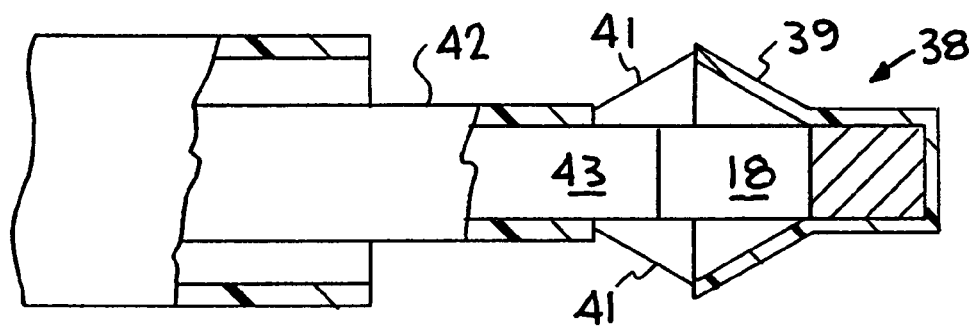
FIG. 11 shows an enhancement to the basic design.
Figure 12:
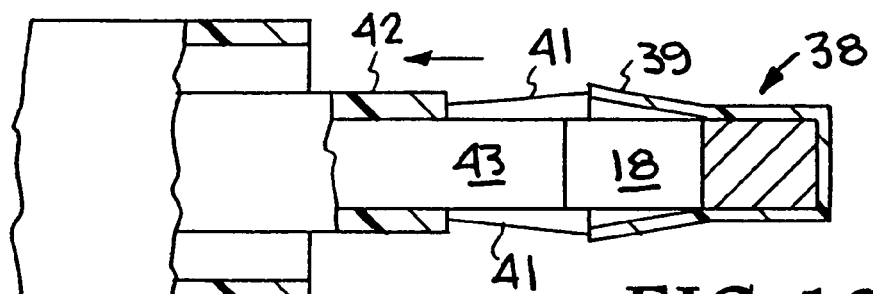
FIG. 12 shows an enhancement to the basic design.

Referring now to FIGS. 11 and 12, the use of a tether 41 to close the expanded SMP actuator 38 is shown. The proximal end of the SMP 39 may be tethered such that tension on the tethers 41 results in the partial and/or complete collapse of the SMP (e.g. Reversible actuation, as shown in FIGS. 11 and 12.) This tethering may be accomplished by using connectors, similar to materials described above, that run parallel to the z-axis. The tethers may be actuated by attaching their proximal end to a second tube 42 that may slide over the fiber optic 43.

Figure 13:
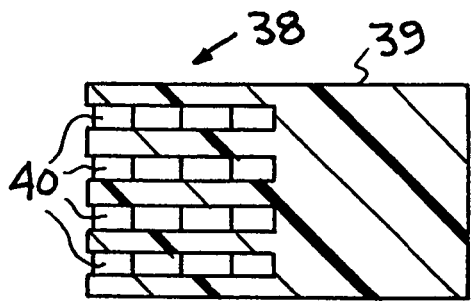
FIG. 13 shows an enhancement to the basic design.
Figure 14:
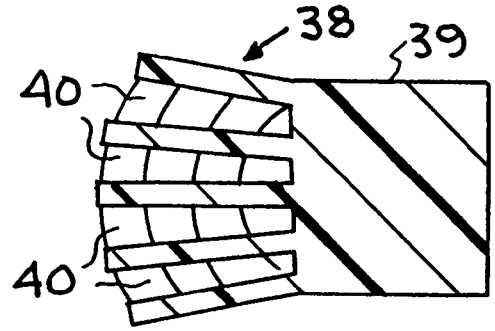
FIG. 14 shows an enhancement to the basic design.

Referring to FIGS. 13 and 14, other systems for collapsing the SMP actuator 38 can be employed. Cutting away axial sections 40 of the material 39 of the SMP actuator 38 would also result in a collapsed state with a low cross-sectional area as show in FIGS. 13 and 14. The resulting radial sections are then connected along their circumference by wires or thread that would make the expanded actuator look more like a basket than an umbrella. The connective material may be located at multiple locations along the z-axis and may be attached to the SMP "petals" by adhesives, embedding or sandwiching the connections between the SMP and another material (possibly SMP).

The collapsing of the SMP can be facilitated by a light source. The collapse of the SMP may be enhanced by turning the light source on. The heating of the SMP while employing a method for collapsing the SMP (such as tethers) and subsequently turning the light source off will result in the SMP holding a second collapsed state. This may be used to contain the blockage between the SMP and diffusing chamber as well as reducing the proximal SMP diameter, which makes retracting through the guide tube more practical. Similarly, if another means were used to open the SMP, such as "pusher" rods instead of "pulling" tethers, then use of light or other heating mechanism to soften the SMP during this process followed by removal of heat will result in the SMP hardening and maintaining an open state. Other means of opening the softened umbrella can be employed including fluidic means (such as gas or liquid flowing from the catheter toward the umbrella to force it into an open state) and electrostatic means (where similar charges on the umbrella and support (ie, fiber) repel one another.

Figure 15A:
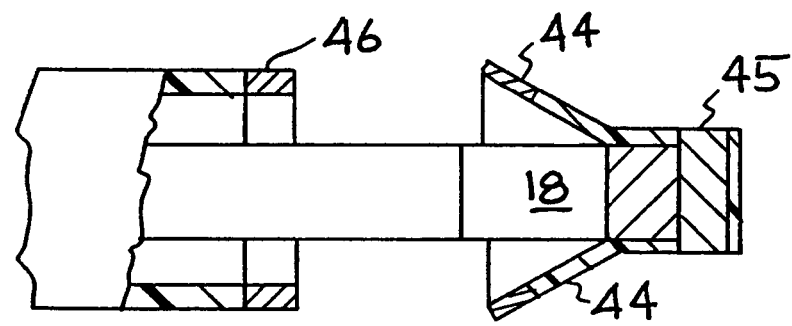
FIGS. 15A, 15B, and 15C illustrate integrating radio-opaque markers into the shape memory polymer actuator.
Figure 15:
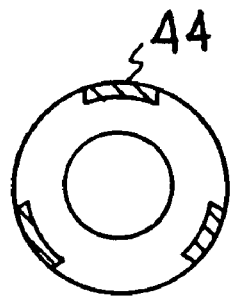
Figure 15C:
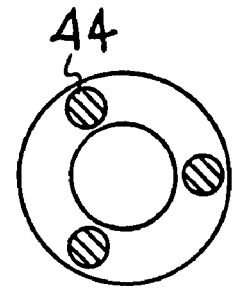

In the case of medical applications of the device, the design may be enhanced by integrating radio-opaque markers 44, 45, and 46 into the SMP as shown in the embodiments shown in FIGS. 15A, 15B, and 15C. These markers 44, 45, and 46 and their relative movement with respect to each other can be used to determine the actuation state of the device (e.g. open or closed). The markers are imaged via fluoroscopy. A minimum of three markers placed symmetrically around the proximal edge of the SMP (e.g. 3 markers—120° separation, 4 markers—90° separation, etc.) would allow the two-dimensional fluoroscopy images to visualize the actuation of the device. FIG. 15B and FIG. 15C show an end view of the SMP 39 with three markers 44 near the outer circumference of the umbrella section. FIG. 15B illustrates circular markers in the umbrella section while the markers in FIG. 15C are arbitrarily shaped. These markers would be either attached to or embedded in the SMP. Their minimal size is dictated by current fluoroscope resolution. Since medical catheters typically have multiple radio-opaque markers, this device is likely to have other marker rings along its length, including one near the distal tip of the device. The device may employ radio-opaque markers for locating the distal and proximal ends of the SMP clot catcher as well as determining if the device is closed for insertion or open for clot entrapment. These radio-opaque markers would be accomplished by localized doping of the SMP with a radio-opaque metal such as platinum or other heavy, yet biocompatible element.

Figure 16:
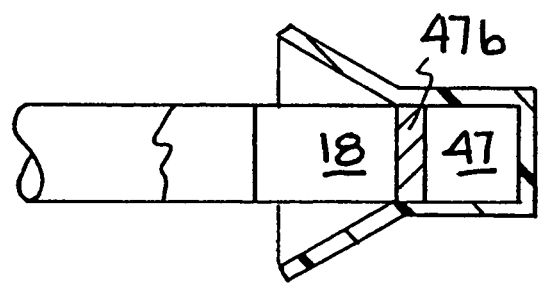
FIG. 16 illustrates a diagnostic sensor at the distal tip of the shape memory polymer actuator.
Figure 17:
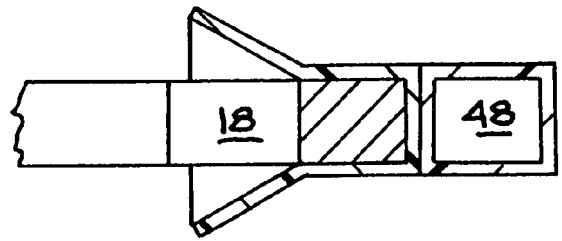
FIG. 17 shows a sensor attached, deposited or embedded in the distal end of the shape memory polymer actuator.

As shown in the embodiment of FIG. 16, the basic device may be enhanced by adding a diagnostic sensor 47 at the distal tip of the actuator. Since the method-of-use includes pushing the device through or around a blockage, a sensor 47 on the distal tip allows for the interrogation of the environment distal to the blockage. In medical applications, for example, this could include a diagnostic that would measure the viability of the distal vessel relative to reinstated blood flow. Since reintroducing blood to necrotic tissue will result in a potentially worse medical condition, a sensor that would help determine the health of the vessel wall would be extremely useful. The sensor may be any type but is likely to be light based. The use of multiple wavelengths and wavelength-specific reflective coatings 47b enable a device to be built that keeps the heating wavelength(s) confined to the diffusing chamber and allows diagnostic wavelengths to pass to the distal tip and back. Alternatively, the same wavelength(s) may be used for both actuating the SMP and interrogating the diagnostic. In this case, instrumentation techniques like heterodyne detection, interference or fluorescence may be useful in isolating the optical changes to the sensor at the distal tip. In the case of an optical sensor, a sensor 48 can be attached, deposited or embedded in the distal end of the device as shown in FIG. 17.

Figure 18:
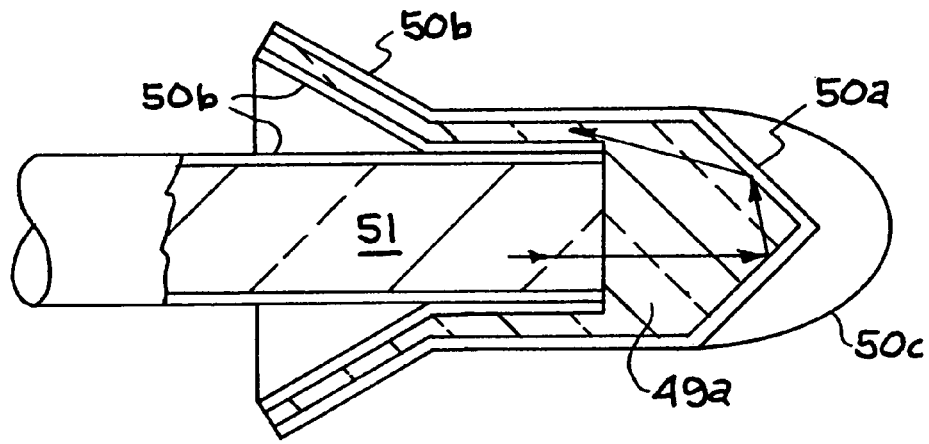
FIG. 18 shows light is coupled directly into the shape memory polymer actuator and aimed at the umbrella section where actuation is required.

As shown in the embodiment of FIG. 18, light is coupled directly into the SMP volume 49a aimed at the umbrella section 49b where actuation is required. A shaped reflector 50a shown in FIG. 18 will aim the light uniformly into the SMP umbrella section 49b and light delivery is maximized by reflective coatings 50b on both the fiber circumference and the SMP. Reflective coatings 50B could exist on all exterior surfaces (making use of any variety of coating techniques) while the internal interface between the fiber end 51 and SMP remains protected from such reflective coating. It is possible to index-match the fiber end 51 with the SMP (possibly using an antireflection layer if the indices of refraction are very different), where this interface surface could also be shaped to enhance uniform illumination in the umbrella portion 49b where it is doped with dye and thus minimize back reflection and maximize absorption. A dome or parabolic cap 50c would likely cover a sharp conical reflecting tip 50a to prevent it from damaging or rupturing blood vessels during transport.

Figure 19:
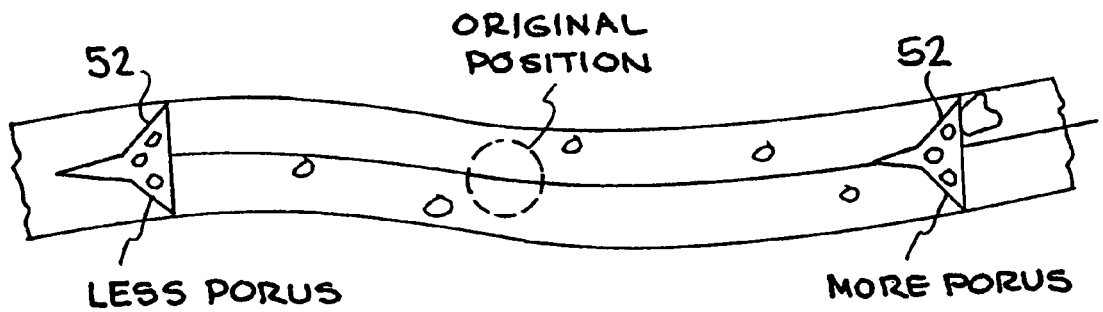
FIG. 19 shows use of multiple umbrellas.

As shown in the embodiment of FIG. 19, multiple umbrellas 52 are used. The final umbrella would likely have the least porosity (or smallest holes for fluid to pass through) to catch the smaller particles. Multiple umbrellas are used to improve the probability of catching all the debris.

Figure 20:
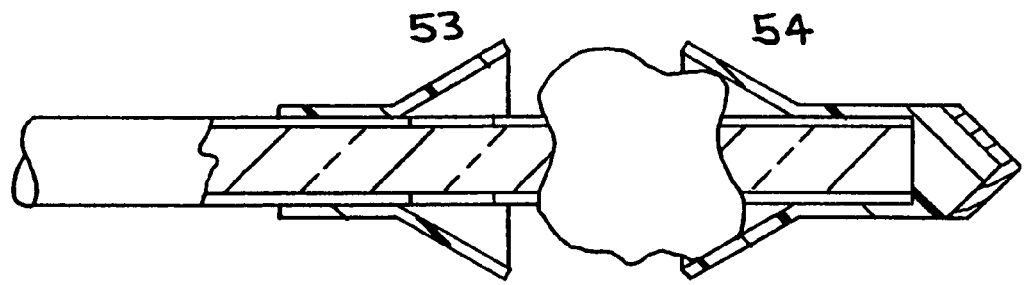
FIG. 20 shows opposing umbrellas used to scrape the walls in both directions to contain more of the debris.

Referring now to FIG. 20, instead of having a guide tube for trapping the blockage (before extraction) it is possible to make use of an opposing SMP umbrella 53 to minimize the initial size of the device and maximize the maneuverability during insertion. The outer rim or edge of the umbrella is strong in only one direction. One could also use the opposing umbrellas 53 and 54 to push back and forth to scrape material off of the walls in both directions and have the debris move into the void between them.

Figure 21:
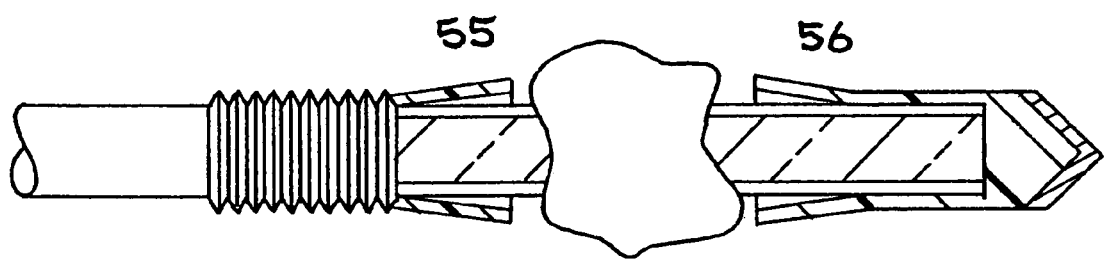
FIG. 21 shows different wavelengths, filters or transition temperatures for independent control of two shape memory polymer actuators.
Figure 22:
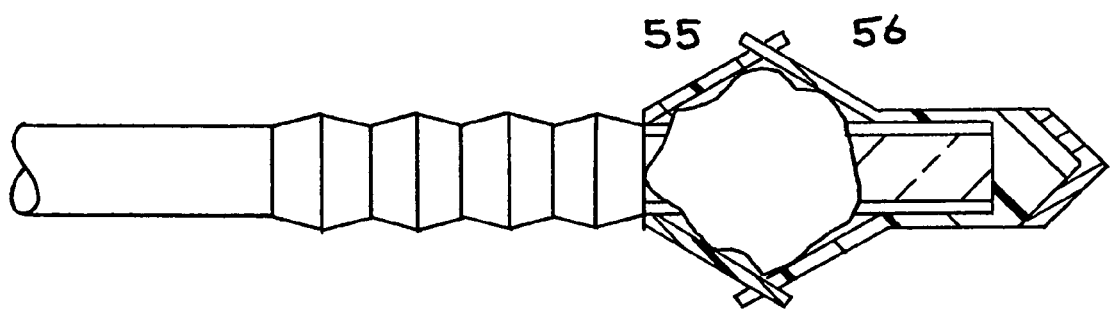
FIG. 22 shows different wavelengths, filters or transition temperatures for independent control of two shape memory polymer actuators.

Opposing umbrellas 53 and 54 can be used to scrape the walls in both directions and contain more of the debris. Ideally the opposing umbrella 53 (shown on the left in FIG. 20) can move and lock with the main umbrella. The opposing umbrella could ride on a separate sleeve with independent illumination means or an SMP device could cause the translation, eliminating the need for axial translations between the fiber and a sleeve or tube. The SMP method is illustrated in FIGS. 21 and 22. Different wavelengths and filters or having different transition temperatures would enable independent control of the two SMP devices. The same or different wavelengths can be used with the two SMP devices 55 and 56 shown (with the same or different transition temperatures) to actuate the umbrellas and interlock to enclosed the material that is to be extracted.

Figure 23:
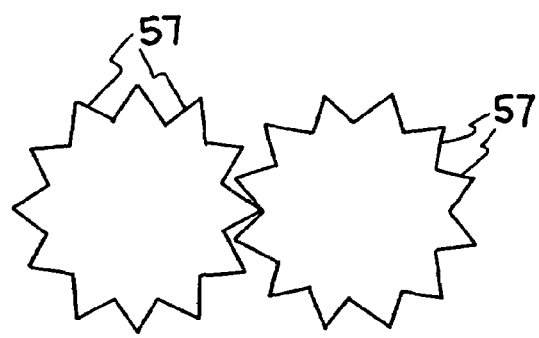
FIG. 23 shows end views of two umbrellas illustrating how the teeth along the outer rim of the two umbrellas interlock and provide improved scraping.
Figure 24:
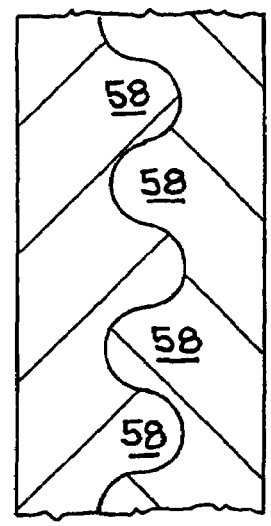
FIG. 24 shows teeth along the outer rim of an umbrella for easy interlocking and improved scraping.

FIG. 23 shows end views of the two umbrellas positioned adjacent each other to illustrate how the teeth along the outer rim of the two umbrellas interlock and provide improved scraping. Teeth 57 and 58 along the outer rim of the umbrella can make for easy interlocking and may be designed for improved scraping. FIG. 23 shows a triangular tooth design 57. FIG. 24 shows the two umbrellas positioned together illustrating how the teeth along the outer rim of the two umbrellas interlock. FIG. 24 shows a rounded tooth design 58.

Figure 25:
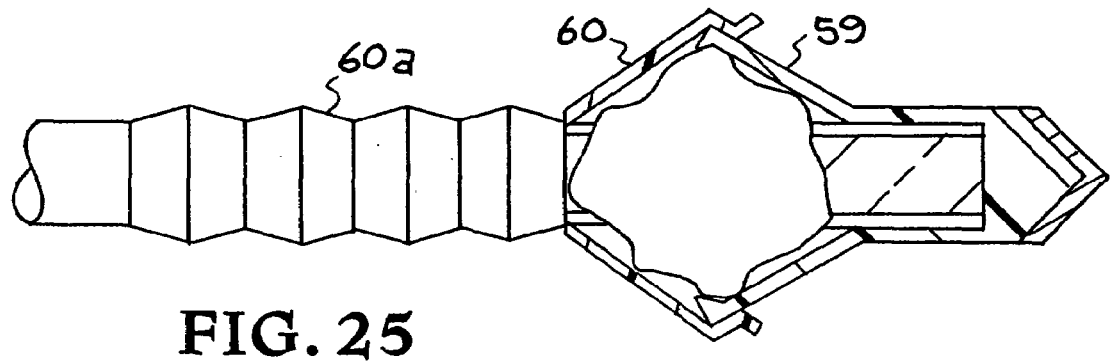
FIG. 25 shows a snap type locking system where the rim of one cone snaps into the rim of the other to enclose the debris through optical actuation.

FIG. 25 shows a snap type locking method where the rim of one cone 59 snaps into the rim of the other cone 60 to enclose the debris through optical actuation. The cones 59 and 60 are forced together by the expanding sleeve 60*a* and the rim of one cone 59 snaps into the other cone 60.

Figure 26:
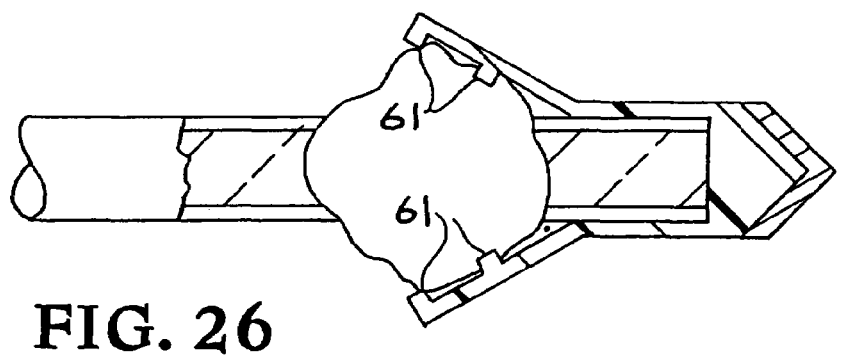
FIG. 26 shows barbs inside and along the rim help to hook and hold the debris.

Another embodiment, shown in FIG. 26, includes a barbed design 61 inside the umbrella. This will hook the obstruction and reduce the possibility of its escape. The barbs 61 inside and along the rim help to hook and hold the debris.

Figure 27:
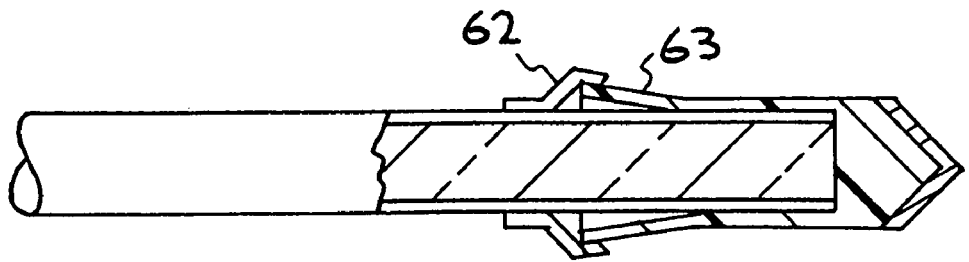
FIG. 27 shows a clamp holding the umbrella closed during transport.
Figure 28:
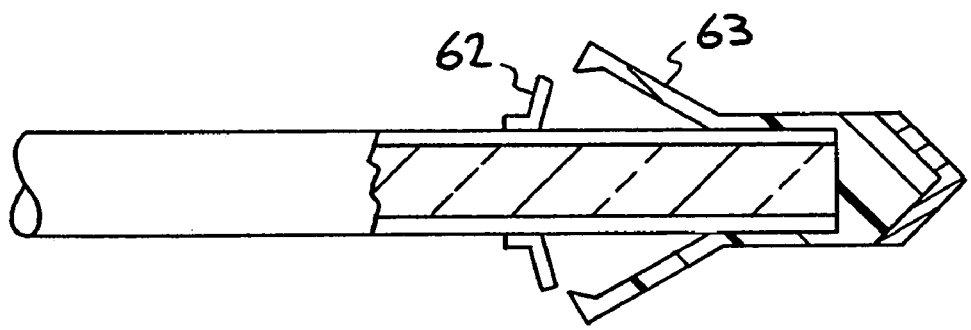
FIG. 28 shows the umbrella opened.

Another embodiment, shown in FIGS. 27 and 28, includes an SMP clamp 62 utilized to hold the pre-opened umbrella 63 in its closed position throughout transport. This allows for positive and negative axial translation of the device through the passageways without opening the umbrella. The clamp 62 holds the umbrella 63 closed during transport. The clamp 62 is opened and the pre-opened umbrella 63 is allowed to move to its expanded state. An SMP is used to release the clamp 63.

Figure 29:
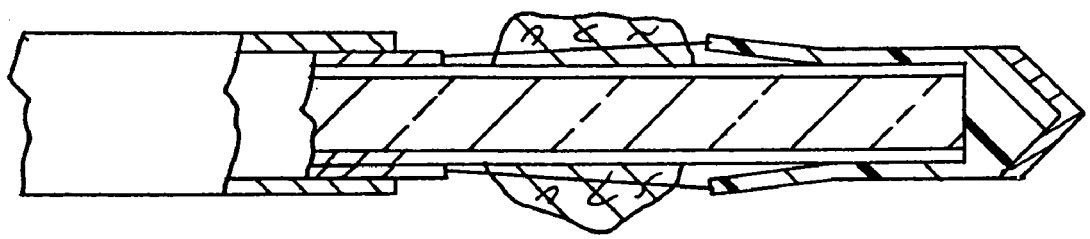
FIG. 29 shows an undesired effect of tethers.
Figure 30:
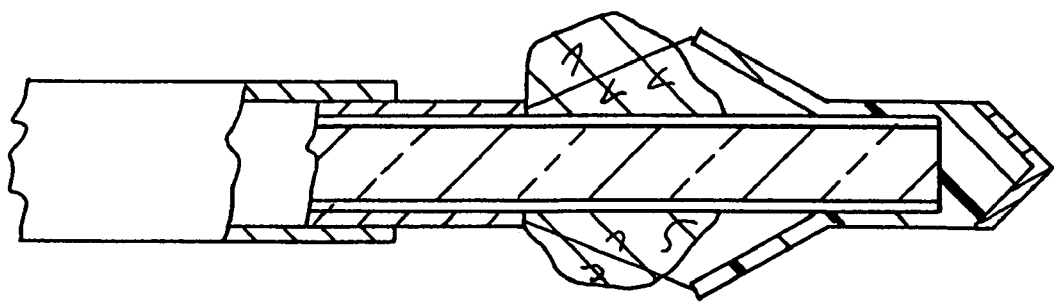
FIG. 30 shows an undesired effect of tethers.
Figure 31:
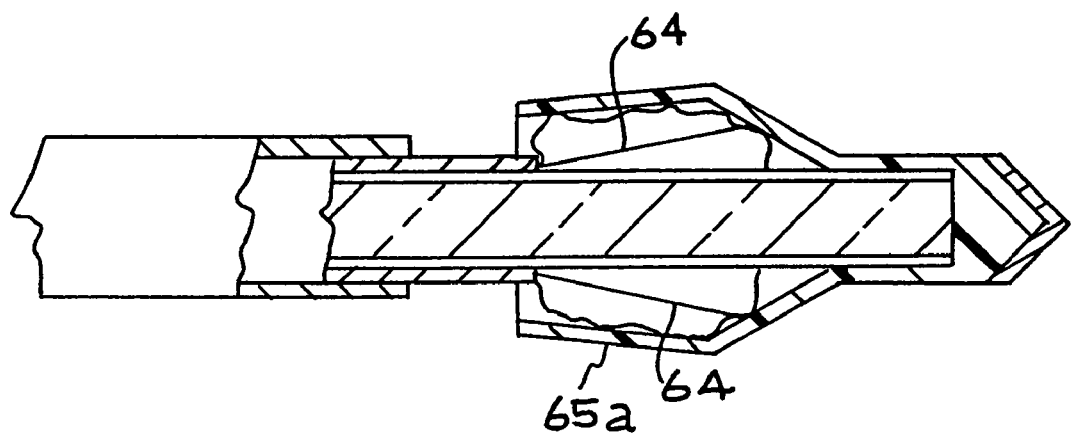
FIG. 31 shows an improvement on tethers.

Tethers were mentioned in the embodiments illustrated in FIGS. 11 and 12. An undesired effect of tethers is illustrated in FIGS. 29 and 30 where the tethers push the debris away. As illustrated in FIGS. 29 and 30, these tethers would have to cut through or circumvent the blockage to be helpful. Failure to do so could actually eject the blockage. Another embodiment that includes a tether 64 is illustrated in FIG. 31. An extension section 65*a* of the umbrella prevents the debris from being ejected as it closes down on the blockage when tether 64 is pulled.

Figure 32:
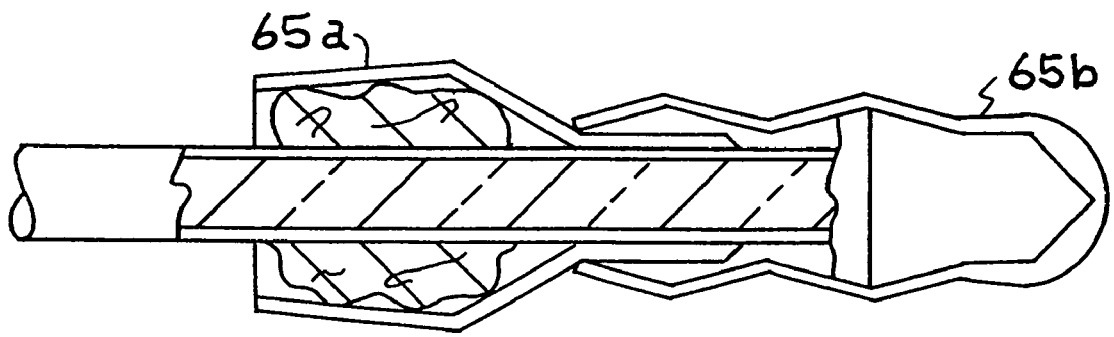
FIG. 32 shows independent control of two shape memory polymer actuators.

Referring now to FIG. 32, a second SMP device 65*b* could be use to close an opened umbrella. The second SMP 65*b* could have a different transition temperature but for more independent control of the SMPs, different wavelengths or polarizations of light could be used in conjunction with filters or polarizers. In general, maintaining polarization in fibers is problematic and control at the output end with polarizers and electronically controlled retarders make the system even more complex. Using two different wavelengths to open then close the umbrella is illustrated in FIG. 32 where an elongating sleeve puts pressure on the umbrella for closure. The second SMP device 65*b*, shown here as an elongating sleeve, puts pressure on the umbrella to close it around the debris.

Bistability was mentioned in regards to using tethers to close the umbrella. The device in FIG. 32 is bistable without tethers. If you heat both SMPs until they become soft, then depending on which cools first decides the mechanical state they will end up in. For example, turn the umbrella actuating light off first and it cools first, pushing away the sleeve and assuming an open umbrella shape. Turn off the closure device light first and the closure device pushes on the umbrella to close it somewhat. Turn on the umbrella actuating light and now you can completely close and encapsulate the now soft umbrella.

Figure 33:
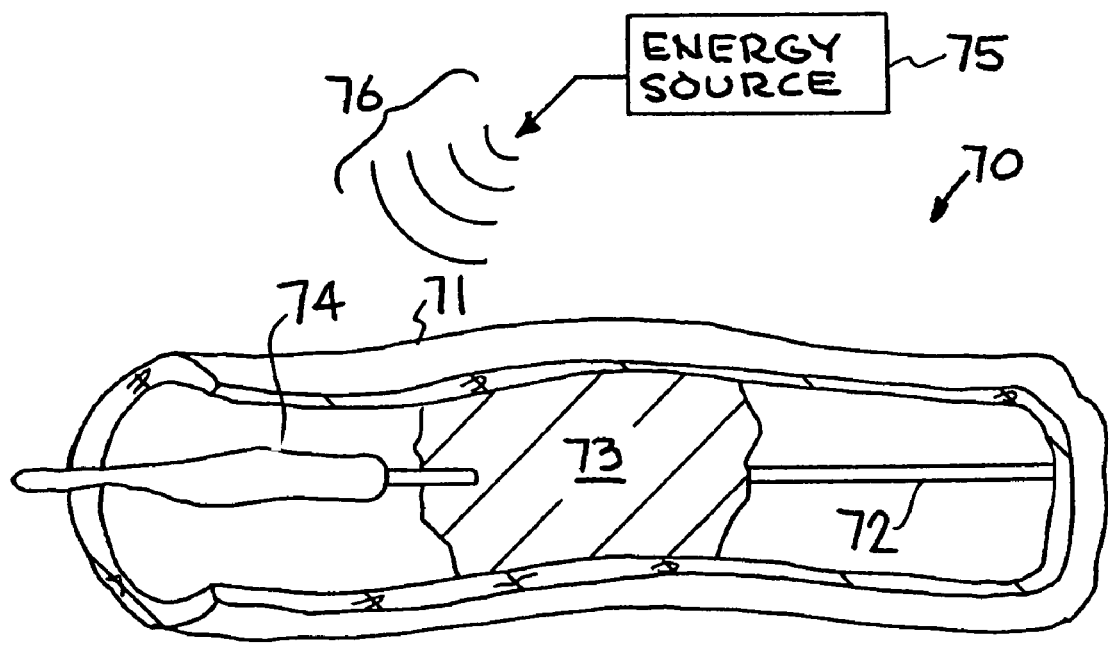
FIG. 33 is a conceptual illustration of another embodiment of the present invention in a vessel with a blockage such as a blood clot.

Referring now to FIG. 33 another embodiment of a system, generally designated by the reference numeral 70, for heating the SMP is shown. A vessel 71 contains a blockage 73. The blockage 73 could be a blood clot, plaque, other emboli, or other blockage. A support structure 72 with a shape memory material actuator 74 on its distal end is inserted through or around the blockage 73. The shape memory material actuator 73 is used to remove the blockage 73 from the vascular system. Actuation is achieved by heating the shape memory material 74.

The shape memory material can be heated using various systems. These systems include induced resistive heating by an external wave field, such as by an associated magnetic or radio frequency (RF) source, external heating through electrical induction or electrothermal heating, with local or remote ultrasonics or other acoustic means of energy transfer, or by converting optical energy into thermal energy that allows the stored energy in the shape memory material to be released. An external energy source 75 transmits energy, in the form of waves 76, to the SMP actuator 74. The external source 75 may produce heating by an external wave field, such as by an associated magnetic or radio frequency (RF) source, or by remote ultrasonics or other acoustic means of energy transfer. The energy is absorbed by the shape memory material and converted into thermal energy that heats the shape memory material above its transition temperature and the shape memory material moves to its primary shape, resulting in mechanical actuation. When the shape memory material actuator 74 is drawn backward it results in the removal of the blockage 73 from the vessel 71.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method of manufacturing an actuator system for acting upon a blockage in a vessel of a vascular system, comprising the steps of:

providing a catheter adapted to be moved through the vessel to the blockage, providing an optical fiber with a distal end, said optical fiber adapted to be carried by said catheter, providing a diffusing chamber connected to said distal end of said optical fiber, processing a shape memory polymer material so that it will expand into a somewhat umbrella shape upon being activated and act on the blockage, operatively connecting said shape memory polymer material to said distal end of said optical fiber and to said diffusing chamber, providing an optical source that provides light energy through said optical fiber to said diffusing chamber and to said shape memory polymer material to activate said shape memory polymer material so that it will expand into a somewhat umbrella shape and act on the blockage, and connecting said optical source to said optical fiber to provide light energy through said optical fiber to said diffusing chamber and to said shape memory polymer material to activate said shape memory polymer material so that it will expand into a somewhat umbrella shape and act on the blockage.

2. The method of manufacturing an actuator for acting upon a material in a vessel of claim 1 wherein said step of processing a shape memory polymer material so that it will expand into a somewhat umbrella shape upon being activated, includes, heating said shape memory polymer material above its melting temperature during processing.

3. The method of manufacturing an actuator for acting upon a material in a vessel of claim 1 wherein said shape memory polymer material has a primary shape before being activated and said step of processing a shape memory polymer material so that it will expand into a somewhat umbrella shape upon being activated, includes, polymerizing said shape memory polymer material while in its primary shape.

4. The method of manufacturing an actuator for acting upon a material in a vessel of claim 2 wherein said shape memory polymer material possesses a glass transformation temperature (Tg) above which the material enters a reversible glassy phase where it becomes soft and flexible and easy to reshape the material and will return to its primary shape if not subjected to undue pressure and once cooled below Tg, the shape is frozen in place and the material becomes hardened and will hold its shape until it is intentionally relaxed by heating the SMP above Tg again.

* * * * *